United States Patent [19]

Kleemann et al.

[11] 4,426,532
[45] Jan. 17, 1984

[54] α-(3-CYANO-PROPANOYL)-AMINOCARBOXYLIC ACID DERIVATIVES

[75] Inventors: Axel Kleemann, Hanau; Jurgen Martens, Alzenau; Horst Weigel, Rodenbach, all of Fed. Rep. of Germany

[73] Assignee: Degussa AG, Frankfurt, Fed. Rep. of Germany

[21] Appl. No.: 381,876

[22] Filed: May 25, 1982

[30] Foreign Application Priority Data

Jun. 19, 1982 [DE] Fed. Rep. of Germany ....... 3124091

[51] Int. Cl.³ .................. C07D 233/64; C07C 121/52
[52] U.S. Cl. ............................. 548/344; 260/465 D; 260/465.4
[58] Field of Search .................. 348/344; 260/465 D, 260/465.4

[56] References Cited

U.S. PATENT DOCUMENTS 3,673,235 6/1972 Burk ................................ 260/465.4
3,810,934 5/1974 O'Murchu ...................... 260/465 D

FOREIGN PATENT DOCUMENTS 2634288 2/1977 Fed. Rep. of Germany .

Primary Examiner—Robert W. Ramsuer
Attorney, Agent, or Firm—Cushman, Darby & Cushman

[57] ABSTRACT

There are prepared specific α-aminocarboxylic acids or their methyl, ethyl, or benzyl esters in which the α-amino group is substituted by a 3-cyanopropanoyl group. The compounds are useful for producing the corresponding derivatives of 4-aminobutyramide ("Gabamide") by catalytic hydrogenation of the cyano group.

10 Claims, No Drawings

α-(3-CYANO-PROPANOYL)-AMINOCARBOXYLIC ACID DERIVATIVES

SUMMARY OF THE INVENTION

The invention is directed to a Nα-(3-cyano-propanoyl)-aminocarboxylic acid derivatives of the general formulae

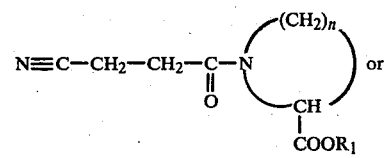

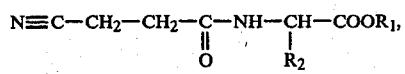

wherein $R_1$ is hydrogen, methyl, ethyl, or benzyl, n is 2, 3, or 4 and $R_2$ is hydrogen or one of the following groups:

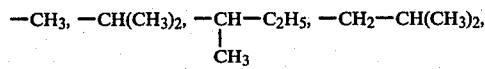

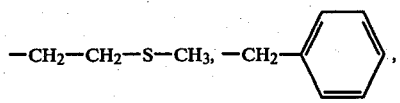

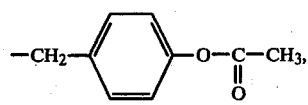

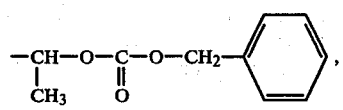

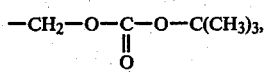

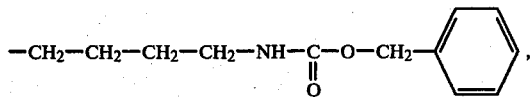

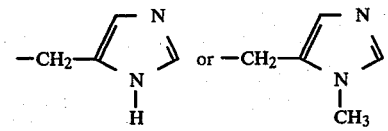

Nα-(3-cyanopropanoyl)-aminocarboxylic acid derivatives of general formulae (I) and (II) are valuable intermediate products for the production of pharmaceuticals. Schiff bases of the aminobutyramide derivatives, prepared by reducing the cyanopropionamide derivatives of the invention and subsequent conversion to the azomethines, have the same uses as those disclosed for the Gabamid derivatives in German Auslegeschrift No. 26 34 288. The hydrochloride salts of the 4-aminobutyramide derivatives also can be used as catalysts for the curing of urea-formaldehyde and melamine-formaldehyde resins, e.g. when used in an amount of 0,1 to 5% of the resin. A further object of the invention therefore ist the use of the Nα-(3-cyanopropanoyl)-aminocarboxylic acid derivatives of the general formulae (I) and (II) for the production of derivatives of 4-aminobutyramide by reduction.

The compounds of the invention can be produced by various processes:

Process A:

3-Cyanopropionic acid is reacted with the appropriate α-aminocarboxylic acid or its methyl, ethyl, or benzyl ester in the presence of a coupling agent, such as dicyclohexylcarbodiimide. Thereby there can be employed as solvents halohydrocarbons such as dichloromethane, chloroform, or carbon tetrachloride; ethers such as diethyl ether, diisopropyl ether, methyl-tert.-butyl ether, dioxane, or tetrahydrofuran; nitriles such as acetonitrile; or aromatic hydrocarbons such as benzene or toluene. The reaction suitably takes place at a temperature between −20° and +20° C., preferably between −10° and +10° C.

Process B:

3-Cyanopropionic acid is first converted into its anhydride or a mixed anhydride, for example with acetic acid, or into the corresponding acid chloride or activated by means of the Woodward-Reagent K, N-ethoxycarbonyl-2-ethoxy-1,2-dihydroquinoline and then reacted with the appropriate α-aminocarboxylic acid or its methyl, ethyl, or benzyl ester. Thereby it is advantageous to have present a base, for example, caustic soda or a tertiary amine such as pyridine, 4-(dimethylamino)-pyridine or triethylamine.

A review of known acylation processes which can be used in the present connection is contained in Houben-Weyl, Methoden der Organischen Chemie, Vol. XV, Part II, (1974), pages 1 et seq.

In a preferred illustrative form of Process B the 3-cyanopropionic acid is converted by reaction with thionyl chloride or oxalyl chloride into the corresponding acid chloride and this reacted in the presence of aqueous sodium hydroxide with the α-aminocarboxylic acid or its ester. The reaction takes place suitably at a temperature between −20° and +50° C., preferably between −20° and +30° C.

Process C:

3-Cyanopropionic acid esters of the general formula

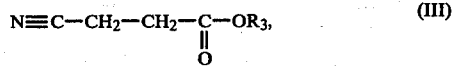

in which $R_3$ is a straight or branched alkyl group having 1 to 6 carbon atoms is reacted with the appropriate α-aminocarboxylic acid or its methyl, ethyl, or benzyl ester. The reaction takes place under heating, preferably under reflux. It can be carried out in the absence of an additional solvent or in the presence of such solvent, for example, of benzene, toluene, or xylene.

Process D:

Nα-acryloyl-aminocarboxylic acid derivatives of the general formulae

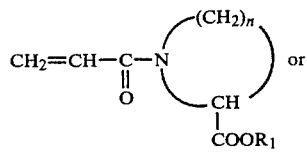

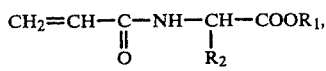

in which $R_1$, $R_2$, and n are as defined above are reacted with hydrocyanic acids in such manner than the HCN adds on to the double bond of the acrylic acid residue. The addition takes place especially smoothly in the presence of catalytic amounts of an alkali metal cyanide, for example, sodium or potassium cyanide. As solvent for this reaction there can be employed, e.g. dimethyl formamide, diethyl formamide, dimethyl acetamide, N-methyl pyrrolidone, tetrahydrofuran, dimethyl sulfoxide, tetramethylene sulfone (sulfolane) or tetramethyl urea and its homologues with up to 8 carbon atoms. The reaction suitably takes place at a temperature between 20° and 150° C., preferably between 70° and 120° C. The pressure has no detectable influence on the speed of reaction and the composition of the reaction mixture after the end of the reaction. The reaction advantageously can be carried out in such manner that there is present a suspension of the catalyst in a portion of the solvent and there is slowly fed in a solution of the Nα-acryloyl-amino-carboxylic acid derivative of the general formula (IV) or (V) and the hydrocyanic acid in the remainder of the solvent. However, just as well there can also be present a solution of the Nα-acryloyl-aminocarboxylic acid derivative in which the catalyst is suspended and the hydrocyanic acid led in.

In all of the above-mentioned processes A, B, and C insofar as the α-aminocarboxylic acid or its ester contains besides the α-amino group, a further amino group or a hydroxyl group this amino or hydroxyl group naturally must be protected according to the known methods of peptide chemistry, for example, through a benzyloxycarbonyl or tert.-butyloxycarbonyl group.

The Nα-acryloyl-aminocarboxylic acid derivative employed in the above Process D can be obtained from the α-aminocarboxylic acid or its esters through reaction with acrylic acid chloride or methacrylic acid chloride according to the Schotten-Baumann reaction. In this reaction too it is understood that any further amino group or hydroxyl groups present in a given case must also be protected through a protective group.

Examples of compounds of general formula (I) according to the invention are N-(3-cyano-propanoyl)-azetidine carboxylic acid, N-(3-cyano-propanoyl)-proline, N-(3-cyano-propanoyl)-pipecolic acid, as well as their methyl-, ethyl-, and benzyl esters.

Examples of compounds of general formula (II) according to the invention are N-(3-cyano-propanoyl)-glycine, N-(3-cyano-propanoyl)-alanine, N-(3-cyano-propanoyl)-valine, N-(3-cyano-propanoyl)-isoleucine, N-(3-cyano-propanoyl)-leucine, N-(3-cyano-propanoyl) methionine, N-(3-cyano-propanoyl)-phenylalanine, N-(3-cyano-propanoyl)-O-acetyl-tyrosine, N-(3-cyano-propanoyl)-O-(benzyloxy-carbonyl)-threonine, N-(3-cyano-propanoyl)-O-(tert.-butyloxycarbonyl)-serine, Nα-(3-cyano-propanoyl)-Nε-(benzyloxycarbonyl)-lysine, Nα-(3-cyano-propanoyl)-histidine, Nα-(3-cyano-propanoyl)-N-methyl-histidine, as well as their methyl-, ethyl-, and benzyl esters.

The α-aminocarboxylic acids, except glycine, taken as a basis of the compounds of the invention can be present in the D-form, in the L-form or as the racemate.

Derivatives of 4-amino-butramide can be produced suitably from the Nα-(3-cyanopropanoyl)-aminocarboxylic acid derivatives of general formula (I) or (II) by hydrogenating them in the presence of a solvent inert under the reaction conditions, a noble metal catalyst and hydrogen chloride at a temperature between 0° and 150° C. Insofar as $R_2$ in general formula (II) signifies a protective group, normally in the hydrogenation the protective group is also split off so that there is obtained a 4-aminobutyramide which also exhibits a further free functional group.

Generally in the hydrogenation first there is formed the hydrochloride of the 4-aminobutyramide derivative which in a given case in a very simple manner, e.g. by treatment with a basic ion exchange resin or with a suitable base, can be converted into the free 4-aminobutyramide derivative.

The hydrogenation takes place in the presence of a solvent inert under the conditions of the hydrogenation reaction. Suitable solvents are water, primary or secondary alcohols having up to 6 carbon atoms, preferably 1 to 3 carbon atoms or their mixtures with each other or with water. The amount of solvent employed is not critical, however, suitably it should be so regulated that the Nα-(3-cyanopropanoyl)-aminocarboxylic acid derivative employed is completely dissolved at the reaction temperature chosen. Especially preferred solvents are water, methanol, ethanol or isopropyl alcohol. Furthermore, the hydrogenation requires the presence of a noble metal catalyst, e.g. palladium, rhodium, or especially a platinum metal catalyst. Especially preferred catalysts are metallic platinum and platinum IV oxide. There can also be employed just as well mixtures of several noble metals or mixtures of noble metals with platinum IV oxide. The catalysts can be used in the free form or as catalysts on carriers (e.g. precipitated on activated carbon). After the end of the hydrogenation they can be recovered and again employed without further purification, whereby in the case of platinum IV oxide it is unimportant whether this is present after the first use partially or completely reduced to $Pt^{2+}$ compounds or metallic platinum. The amount of noble metal catalyst employed is not critical. However, it is recommended for obtaining shorter hydrogenation times to employ the noble metal catalysts in such amount that the weight ratio between the Nα-(3-cyanopropanoyl)aminocarboxylic acid derivative employed and the catalyst is from 300:1 to 1:1, preferably 100:1 to 5:1.

Finally the hydrogenation takes place in the presence of hydrogen chloride, which suitably is used in equimolar amount to the Nα-(3-cyanopropanoyl)-aminocarboxylic acid derivative employed. However, the use of a slight excess of hydrogen chloride is also possible.

The hydrogenation takes place at a temperature between 0° and 150° C., preferably between 10° and 50° C. It can be carried out without pressure (i.e. without superatmospheric pressure) by leading hydrogen through the reaction mixture, or in a pressure resistant reaction vessel under a hydrogen pressure up to 100 bar. Preferably, the hydrogenation takes place at pressures up to 20 bar. The hydrogen pressure to be sure has a certain influence on the time required for the complete hydrogenation which is somewhat shortened with increasing pressure, but has scarcely any influence on the purity of the 4-aminobutyramide derivative formed.

Unless otherwise indicated all parts and percentages are by weight.

The process can comprise, consist essentially of, or consist of the stated steps with the materials set forth.

The invention is further explained in connection with the following examples.

DETAILED DESCRIPTION

EXAMPLE 1

A solution of 26.9 grams (0.15 mole) of L-phenylalanine methyl ester in 200 ml of dichloromethane was treated successively dropwise at 0° C.

(a) with a solution of 30.9 grams of N,N'-dicyclohexylcarbodiimide in 75 ml of dichloromethane and (b) with a solution of 14.9 grams (0.15 mole) of 3-cyanopropionic acid in 30 ml of dichloromethane. The mixture was allowed to stand overnight and the precipitate which came out was filtered. The filtrate was washed with water, dried, filtered and the solvent removed on a rotary evaporator. The residue was recrystallized from a mixture of ethyl acetate and petroleum ether. There were obtained 26.8 grams (68.6% of theory) of N-(3-cyanopropanoyl)-L-phenylalanine methyl ester. Melting Point: 71°–72° C.

$\alpha_D^{20} = +12.2°$ (c=4 in Methanol)
Elemental Analysis: $C_{14}H_{16}N_2O_3$ (260.29)

|   | Calculated (%): | Found (%): |
|---|---|---|
| C | 64.60 | 65.00 |
| H | 6.20 | 5.99 |
| N | 10.76 | 10.89 |

IR-Spectrum (neat): $\nu(-C\equiv N)$ 2270 cm$^{-1}$.

EXAMPLE 2

26 grams (0.1 mole) of N-(3-cyanopropanoyl)-L-phenylalanine methyl ester were dissolved in 150 ml of ethanol which contained 0.1 mole of hydrogen chloride and hydrogenated with hydrogen in the presence of 0.8 gram of platinum IV oxide at normal pressure and 30° to 35° C. After 1½ hours the theoretically calculated amount of hydrogen was taken up. The catalyst was filtered off and the filtrate evaporated to dryness. The residue remaining was stirred for 2 hours with 0.2 mole of NaOH in ethanol/water to split off the ester group. In the neutralization to pH6 a colorless precipitate of N-(4-aminobutyryl)-L-phenylalanine crystallized out.

Yield: 19.6 grams (78.4% of theory)
Melting Point: 225°–226° C.
$\alpha_D^{20} = +32.6°$ (c=1 in water)
The material reacted positive to ninhydrin.

EXAMPLE 3

Example 1 was repeated with the single difference that in place of L-phenylalanine methyl ester there was treated the D-phenylalanine methyl ester.
Yield of N-(3-cyano-propanoyl)-D-phenylalaninemethyl
ester: 26.9 grams (68.9% of theory)
Melting Point: 72°–73° C.
$\alpha_D^{20} = -12.1°$ (c=4 in methanol)
IR-Spectrum (neat): $\nu(-C\equiv N)$ 2270 cm$^{-1}$.

EXAMPLE 4

Example 2 was repeated with the single difference that in place of N-(3-cyanopropanoyl)-L-phenylalanine methyl ester there was employed the D-isomer. There were obtained 20.1 grams (80.4% of theory) N-(4-amino-butyryl)-D-phenylalanine,
Melting Point: 224°–225° C.
$\alpha_D^{20} = -31.9°$ (c=1 in water)
The material reacted positive to ninhydrin.

EXAMPLE 5

Example 1 was repeated with the single difference that in place of the L-phenylalanine methyl ester there was employed the D,L-phenylalanine methyl ester.
Yield of N-(3-cyano-propanoyl)-D,L-phenylalanine methyl ester: 22.1 grams (56.6% of theory)
Elemental analysis: $C_{14}H_{16}N_2O_3$ (260,29)

|   | Calculated (%): | Found (%): |
|---|---|---|
| C | 64.60 | 64.29 |
| H | 6.20 | 5.99 |
| N | 10.76 | 10.81 |

IR-Spectrum (neat): $\nu(-C\equiv N)$ 2270 cm$^{-1}$.

EXAMPLE 6

The procedure was as in Example 1. In place of the L-phenylalanine methyl ester there were employed 24.8 grams (0.15 mole) of L-histidine methyl ester. The N$\alpha$-(3-cyanopropanoyl)-L-histidine methyl ester crystallized out together with the N,N-dicyclohexyl urea and after the filtering off was separated from the latter by extraction with warm acetone. The acetone was distilled off. The product was recrystallized from fresh acetone.
Yield: 18.2 grams (48.5% of theory)
Melting Point: 133°–135° C.
IR-Spectrum (neat): $\nu(-C\equiv N)$ 2250 cm$^{-1}$; $\nu(-COOR)$ 1730 cm$^{-1}$; $\nu(-CO-N<)$ 1650 cm$^{-1}$.

EXAMPLE 7

The procedure was as in Example 1. In place of the L-phenylalanine methyl ester there were employed 19.4 grams (0.15 mole) of L-proline methyl ester. Yield of N-(3-cyanopropanoyl)-L-proline methyl ester: 21.5 grams (68% of theory) as a colorless to yellowish oil.
Thin Layer chromatogram (SiO$_2$; Mobile phase n-butanol:glacial acetic acid:water=4:1:1):R$_F$=0.53
IR-Spectrum (KBr): $\nu(-C\equiv N)$ 2245 cm$^{-1}$; $\nu(-COOR)$ 1745 cm$^{-1}$; $\nu(-CO-N<)$ 1650 cm$^{-1}$

EXAMPLE 8

Example 2 was repeated with the single difference that in place of N-(3-cyanopropanoyl)-L-phenylalanine methyl ester there was employed 0.1 mole of N-(3-cyanopropanoyl)-L-proline methyl ester.
The yield of N-(4-aminobutyryl)-L-proline.HCl was 12.5 grams (52.9% of theory). The material is positive to ninhydrin. In the IR spectrum (KBr) there was no longer detectable a nitrile band.

EXAMPLE 9

Example 7 was repeated with the single difference that in place of the L-proline methyl ester there was employed the same amount by weight of the D-proline methyl ester. Yield of N-(3-cyanopropanoyl)-D-proline methyl ester: 23.0 grams (73% of theory).

Thin layer chromatogram (SiO$_2$; mobile phase=n-butanol:glacial acetic acid:water=4:1:1):R$_f$=0.53.

EXAMPLE 10

The procedure was as in Example 1. In place of L-phenylalanine methyl ester there were employed 55.6 grams (0.15 mole) of Nε-(benzyloxycarbonyl)-L-lysine benzyl ester. The oily residue remaining after the evaporation of the dichloromethane crystallized out in triturating with diethyl ether/petroleum ether.

Yield of Nα-(3-Cyano-propanoyl)-Nε-(benzyloxycarbonyl)-L-lysine-benzyl ester: 45 grams (66.7% of theory)

Melting Point: 41°–43° C.

α$_D^{20}$ = −18.7° (c=2 in methanol)

IR-Spectrum (neat): ν(—C≡N) 2245 cm$^{-1}$; ν(—COOR) 1740 cm$^{-1}$ (broad); ν(—CO—N<) 1685 and 1655 cm$^{-1}$.

EXAMPLE 11

The procedure was as in Example 10 with the single difference that in place of the Nε-(benzyloxycarbonyl)-L-lysine benzyl ester there was employed 55.6 grams (0.15 mole) of Nε-(benzyloxycarbonyl)-D-lysine-benzyl ester.

Yield of Nα-(3-cyano-propanoyl)-Nε-(benzyloxycarbonyl)-D-lysine-benzyl ester: 49.5 grams (73.4% of theory)

Melting Point: 42°–44° C.

α$_D^{20}$ = +18.6° (c=2 in methanol).

The entire disclosure of German priority application No. P 3124091.7 is hereby incorporated by reference.

What is claimed is:

1. An Nα-(3-cyanopropanoyl)-aminocarboxylic acid derivative of the formula $$N\equiv C-CH_2-CH_2-\underset{\underset{O}{\|}}{C}-NH-\underset{\underset{R_2}{|}}{CH}-COOR_1, \quad (II)$$

where R$_1$ is hydrogen, methyl, ethyl, or benzyl and R$_2$ is hydrogen or

—CH$_3$, —CH(CH$_3$)$_2$, —CH—C$_2$H$_5$, —CH$_2$—CH(CH$_3$)$_2$,
                              |
                              CH$_3$

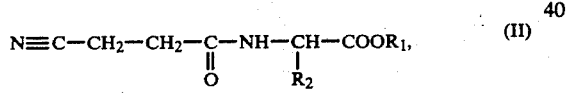

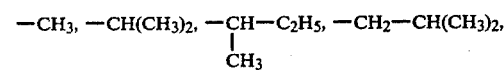

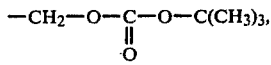

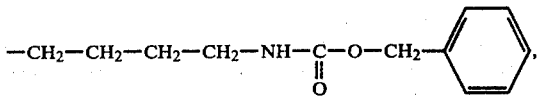

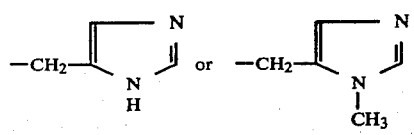

2. A compound according to claim 1 where R$_1$ is hydrogen.

3. A compound according to claim 1 where R$_2$ is

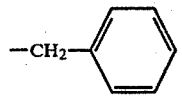

4. A compound according to claim 1 where R$_2$ is

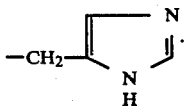

5. A compound according to claim 1 where R$_1$ is methyl, ethyl, or benzyl.

6. A compound according to claim 5 where R$_2$ is

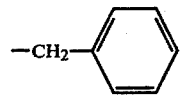

7. A compound according to claim 6 where R$_1$ is methyl.

8. A compound according to claim 5 where R$_2$ is

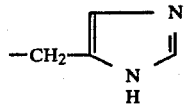

9. A compound according to claim 8 where R$_1$ is methyl.

10. A compound according to claim 5 where R$_2$ has the formula

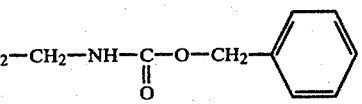

and R$_1$ is benzyl.

UNITED STATES PATENT AND TRADEMARK OFFICE
CERTIFICATE OF CORRECTION

PATENT NO. : 4,426,532
DATED : January 17, 1984
INVENTOR(S) : KLEEMANN ET AL

It is certified that error appears in the above-identified patent and that said Letters Patent is hereby corrected as shown below:

In The Cover Sheet:

Item [30], June 19, 1982 should be June 19, 1981

Signed and Sealed this

Eighth Day of May 1984

[SEAL]

Attest:

GERALD J. MOSSINGHOFF

Attesting Officer

Commissioner of Patents and Trademarks